United States Patent [19]
Rheinheimer et al.

[11] Patent Number: 5,326,744
[45] Date of Patent: Jul. 5, 1994

[54] GLYCOL ALDEHYDE AND LACTIC ACID DERIVATIVES AND THE PREPARATION AND USE THEREOF

[75] Inventors: Joachim Rheinheimer, Ludwigshafen; Ernst Baumann, Speyer; Uwe J. Vogelbacher, Ludwigshafen; Thomas Saupe, Sandhausen; Matthias Bratz, Speyer; Norbert Meyer, Ladenburg; Matthias Gerber, Mutterstadt; Karl-Otto Westphalen, Speyer; Helmut Walter, Obrigheim; Uwe Kardorff, Mannheim, all of Fed. Rep. of Germany

[73] Assignee: BASF Aktiengesellschaft, Ludwigshafen, Fed. Rep. of Germany

[21] Appl. No.: 994,252

[22] Filed: Dec. 21, 1992

[30] Foreign Application Priority Data

Dec. 21, 1991 [DE] Fed. Rep. of Germany ....... 4142570

[51] Int. Cl.$^5$ .................... C07D 405/02; A01N 43/54
[52] U.S. Cl. .................... 504/241; 544/244; 544/278; 544/117; 544/80; 544/58.5; 540/470; 540/467; 540/481; 540/544; 540/553; 540/575; 540/600
[58] Field of Search ............... 544/244, 278; 504/241

[56] References Cited

U.S. PATENT DOCUMENTS

| | | | |
|---|---|---|---|
| 4,180,577 | 12/1979 | Hamano et al. | 544/278 |
| 4,968,340 | 11/1990 | Kaku et al. | 71/92 |
| 5,098,465 | 3/1992 | Kruger et al. | 71/93 |
| 5,145,960 | 9/1992 | Zahler et al. | 544/244 |

FOREIGN PATENT DOCUMENTS

| | | |
|---|---|---|
| 2017975 | 12/1990 | Canada. |
| 2021486 | 1/1991 | Canada. |
| 92133575 | 9/1990 | European Pat. Off. ............ 544/244 |
| 0400741 | 12/1990 | European Pat. Off.. |
| 0490224 | 6/1992 | European Pat. Off.. |

OTHER PUBLICATIONS

Schulte et al., Chem. Ber., 103 (1970) pp. 1250-1261.

Primary Examiner—Mukund J. Shah
Assistant Examiner—P. K. Sripada
Attorney, Agent, or Firm—Keil & Weinkauf

[57] ABSTRACT

Glycol aldehyde and lactic acid derivatives and their sulfur analogs of the formula I

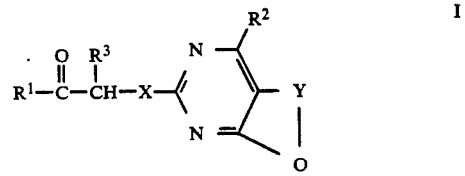

where $R^1$ to $R^3$ have the meanings given in the specification, X is oxygen, sulfur or a single bond, and Y is a $C_2$-$C_4$-alkylene or $C_2$-$C_4$-alkenylene chain where in each case a methylene group may be substituted by an oxo group (=O), environmentally compatible salts of the compounds I, methods of preparing the compounds I, and their use as herbicides.

10 Claims, No Drawings

GLYCOL ALDEHYDE AND LACTIC ACID DERIVATIVES AND THE PREPARATION AND USE THEREOF

The present invention relates to glycol aldehyde and lactic acid derivatives and their sulfur analogs of the formula I

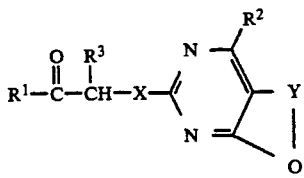

where
$R^1$ is
hydrogen;
succinylimidoxy;
a 5-membered heteroaromatic structure which is bonded via a nitrogen atom, contains two or three nitrogen atoms and may carry one or two halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and or $C_1$–$C_4$-alkylthio; a radical

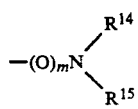

in which m is 0 or 1 and $R^{14}$ and $R^{15}$ are identical or different and are each
hydrogen;
$C_1$–$C_6$-alkyl, $C_3$–$C_6$-alkenyl or $C_3$–$C_6$-alkynyl, where these three radicals may each carry from one to five halogen atoms and/or one or two of the following groups: $C_1$–$C_6$-alkoxy, $C_3$–$C_6$-alkenyloxy, $C_3$–$C_6$-alkynyloxy, $C_1$–$C_6$-alkylthio, $C_3$–$C_6$-alkenylthio, $C_3$–$C_6$-alkynylthio, $C_1$–$C_6$-haloalkoxy, cyano, $C_1$–$C_6$-alkylcarbonyl, $C_3$–$C_6$-alkenylcarbonyl, $C_3$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, bis-$C_1$–$C_6$-dialkylamino, cyclo-$C_1$–$C_6$-alkyl or unsubstituted or substituted phenyl;
unsubstituted or substituted cyclo-$C_3$–$C_6$-alkyl; or unsubstituted or substituted phenyl;
or $R^{14}$ together with $R^{15}$ form an unsubstituted or substituted, cyclized $C_4$–$C_7$-alkylene chain or together form an unsubstituted or substituted, cyclized $C_3$–$C_6$-alkylene chain having a hetero atom selected from the group consisting of oxygen, sulfur and nitrogen;
$R^1$ is furthermore a group

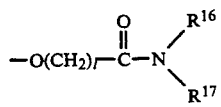

where $R^{16}$ and $R^{17}$ are identical or different and are each hydrogen, $C_1$–$C_6$-alkyl, unsubstituted or substituted phenyl, $C_3$–$C_6$-alkenyl or $C_3$–$C_6$-alkynyl and l is 1, 2, 3 or 4;
$R^1$ is furthermore a group

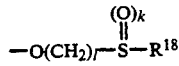

where $R^{18}$ is $C_1$–$C_6$-alkyl, unsubstituted or substituted phenyl $C_1$–$C_6$-haloalkyl, $C_3$–$C_6$-alkenyl or $C_3$–$C_6$-alkynyl, l is 1, 2, 3 or 4 and k is 0, 1 or 2;
$R^1$ is furthermore $OR^5$, where $R^5$ is
(a) hydrogen, an alkali metal cation, one equivalent of an alkaline earth metal cation, the ammonium cation or an organic ammonium ion;
(b) $C_3$–$C_{12}$-cycloalkyl which may carry from one to three $C_1$–$C_4$-alkyl radicals;
(c) $C_1$–$C_{10}$-alkyl which may carry from one to five halogen atoms and/or one of the following radicals: $C_1$–$C_4$-alkoxy, $C_1$–$C_4$-alkylthio, cyano, $C_1$–$C_8$-alkylcarbonyl, $C_3$–$C_{12}$-cycloalkyl, $C_1$–$C_8$-alkoxycarbonyl, phenyl, phenoxy or phenylcarbonyl, where the aromatic radicals in turn may each carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
(d) $C_1$–$C_{10}$-alkyl which may carry from one to five halogen atoms and carries one of the following radicals: a 5-membered heteroaromatic structure containing from one to three nitrogen atoms or a 5-membered heteroaromatic structure containing one nitrogen atom and one oxygen or sulfur atom, which may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
(e) $C_2$–$C_6$-alkyl which carries one of the following radicals in the 2-position: $C_1$–$C_6$-alkoximino, $C_3$–$C_6$-alkenyloximino, $C_3$–$C_6$-haloalkenyloximino or benzyloximino;
(f) $C_3$–$C_6$-alkenyl or $C_3$–$C_6$-alkynyl, where these groups in turn may carry from one to five halogen atoms;
(g) phenyl which may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
(h) a 5-membered heteroaromatic structure which is bonded via a nitrogen atom, contains from one to three nitrogen atoms and may carry one or two halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkythio;
(i) a group —N=$CR^6R^7$, where $R^6$ and $R^7$ are each $C_1$–$C_{20}$-alkyl which in turn may carry phenyl, $C_1$–$C_4$-alkoxy and/or $C_1$–$C_4$-alkylthio; or phenyl; or $R^6$ and $R^7$ together form a $C_3$–$C_{12}$-alkylene chain which may carry from one to three $C_1$–$C_3$-alkyl groups;
$R^1$ is furthermore a radical

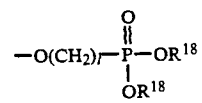

where $R^{18}$ and l have the abovementioned meanings,
$R^1$ is furthermore or a radical

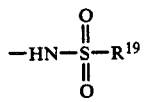

where $R^{19}$ is $C_1$–$C_6$-alkyl or phenyl which in turn may carry from one to four of the following substituents: halogen, nitro, cyano, $C_1$–$C_6$-alkyl;

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^3$ is hydrogen; $C_1$–$C_8$-alkyl, $C_2$–$C_8$-alkenyl, $C_2$–$C_8$-alkynyl, phenyl, $C_3$–$C_8$-cycloalkenyl or $C_3$–$C_8$-cycloalkyl, each of which may carry from one to five halogen atoms and, independently of one another, from one to three of the following substituents:

(i) hydroxyl, $C_1$–$C_4$-haloalkyl, $C_1$–$C_4$-alkoxy, $C_1$–$C_4$-alkylthio, cyano, nitro, $C_1$–$C_4$-alkoxycarbonyl, $C_1$–$C_4$-alkylcarbonyl, $C_1$–$C_4$-alkyl, phenylcarbonyl, $C_3$–$C_{12}$-cycloalkyl, $C_3$–$C_{12}$-cycloalkenyl;

(ii) a 5-membered heterocyclic structure containing no double bonds or one or two double bonds and from one to four nitrogen atoms or one or two nitrogen atoms and additionally one sulfur or oxygen atom, which may carry from one to three halogen atoms and/or from one to three of the following radicals: nitro, cyano, $C_1$–$C_4$-alkyl, $C_1$–$C_4$-alkoxy, $C_1$–$C_4$-alkylthio, $C_1$–$C_4$-haloalkyl or phenyl, which in turn may carry from one to three halogen atoms and/or from one to three methyl groups;

(iii) thienyl which may carry from one to three halogen atoms and/or from one to three of the following radicals: $C_1$–$C_4$-alkyl, $C_1$- or $C_2$-haloalkyl and nitro;

(iv) pyridyl which may carry from one to three halogen atoms and/or from one to three of the following radicals: $C_1$–$C_4$-alkyl, $C_1$- or $C_2$-haloalkyl or nitro;

(v) naphthyl, quinolyl, benzoxazolyl, benzothiazolyl, benzothienyl, indazolyl or benzotriazolyl, each of which may carry from one to three halogen atoms and/or from one to three of the following radicals: $C_1$–$C_4$-alkyl and $C_1$- or $C_2$-haloalkyl;

(vi) phenyl which in turn may carry from one to five halogen atoms and/or from one to three of the following radicals: $C_1$–$C_4$-alkyl, $C_1$–$C_4$-alkoxy, $C_1$–$C_4$-haloalkyl, $C_1$–$C_4$-haloalkoxy, cyano, nitro, $C_1$–$C_4$-dialkylamino and/or $C_1$–$C_4$-alkylthio;

(vii) a 5-membered or 6-membered heterocyclic structure containing no double bonds or one or two double bonds and one or two oxygen or sulfur atoms, which may furthermore carry the following radicals: $C_1$–$C_4$-alkyl, $C_1$–$C_4$-alkoxy, $C_1$–$C_4$-haloalkyl, $C_1$–$C_4$-haloalkoxy or nitro;

$R^3$ may furthermore be a 5-membered or 6-membered heterocyclic structure containing no double bonds or one or two double bonds and from one to four nitrogen atoms or one or two nitrogen atoms and additionally one sulfur or oxygen atom, which may carry from one to three halogen atoms and/or from one to three of the following radicals: nitro, cyano, $C_1$–$C_4$-alkyl, $C_1$–$C_4$-alkylthio, $C_1$–$C_4$-haloalkyl, $C_1$–$C_4$-haloalkoxy, $C_1$–$C_4$-alkoxy or phenyl, which in turn may carry from one to three halogen atoms and/or from one to three methyl groups;

pyridyl which may carry from one to three halogen atoms and/or from one to three of the following radicals: $C_1$–$C_4$-alkyl, $C_1$- or $C_2$-haloalkyl and nitro;

naphthyl, quinolyl, benzoxazolyl, indazolyl or benzotriazolyl, each of which may carry from one to three halogen atoms and/or from one to three of the following radicals: $C_1$–$C_4$-alkyl and $C_1$- or $C_2$-haloalkyl;

a 5-membered or 6-membered heterocyclic structure containing no double bonds or one or two double bonds and one or two oxygen or sulfur atoms, which may furthermore carry the following radicals: halogen, nitro, $C_1$–$C_4$-alkyl, $C_1$–$C_4$-alkoxy, $C_1$–$C_4$-haloalkyl or $C_1$–$C_4$-haloalkoxy;

$R^3$ together with $R^1$ are an unsubstituted or substituted $C_4$–$C_7$-alkylene chain where $CH_2$ may be replaced by oxygen, sulfur or nitrogen;

X is oxygen, sulfur or a single bond and

Y is a $C_2$–$C_4$-alkylene or $C_2$–$C_4$-alkenylene chain where in each case a methylene group maybe substituted by an oxo group ($=O$) and/or the alkylene or alkenylene chain may be substituted by $C_1$–$C_4$-alkyl, phenyl, $C_1$–$C_4$-alkoxy or $C_1$–$C_4$-alkoxycarbonyl;

in the abovementioned cases the expression unsubstituted or substituted meaning in each case that the groups so referred to may carry one or more of the following substituents: halogen, nitro, cyano, $C_1$–$C_6$-alkyl, $C_1$–$C_6$-haloalkyl, $C_1$–$C_6$-alkoxy and $C_1$–$C_6$-alkylthio, and environmentally compatible salts of the compounds I.

The present invention furthermore relates to processes for the preparation of the compounds I and to their use as herbicides and growth regulators.

The literature (EP-A 347 811, EP-A 400 741, EP-A 422 751 and EP-A 409 368) describes herbicidal glycol aldehyde and lactic acid derivatives and their sulfur analogs. However, their action is often unsatisfactory.

It is an object of the present invention to provide novel glycol aldehyde and lactic acid derivatives and their sulfur analogs having improved herbicidal properties and having plant growth-regulating properties.

We have found that this object is achieved by the compounds of the formula I which are defined at the outset. We have also found processes for the preparation of the compounds I and methods for controlling undesirable plant growth with the compounds I. We have furthermore found that glycol aldehyde and lactic acid derivatives of the general formula I defined above have excellent plant growth-regulating properties.

The invention relates both to the racemic compounds I and to the optionally active compounds I (R or S configuration) if $R^3 \neq$ hydrogen.

Compounds of the formula I are obtained, for example, by reacting an appropriately substituted glycol aldehyde or lactic acid derivative of the formula II with a corresponding compound of the formula III in the presence of a base.

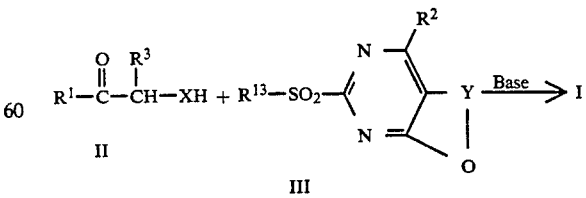

In the formula III, $R^{13}SO_2$ is a conventional nucleofugic leaving group, for example arylsulfonyl, such as phenylsulfonyl or substituted phenylsulfonyl, suitable substituents being one or more, for example from 1 to 3, low molecular weight alkyl or alkoxy radicals, such as $C_1$-$C_4$-alkyl or alkoxy, or halogen, e.g. chlorine, fluorine or bromine; or alkylsulfonyl, such as $C_1$-$C_4$-alkylsulfonyl, e.g. methylsulfonyl, or haloalkylsulfonyl. Alkali metal or alkaline earth metal hydrides, such as NaH and $CaH_2$, alkali metal hydroxides, such as NaOH and KOH, alkali metal alcoholates, such as potassium tert-butylate, alkali metal carbonates, such as $Na_2CO_3$ and $K_2CO_3$, alkali metal amides, such as $NaNH_2$ and lithium diisopropylamide, or tertiary amines may be used as bases. When an inorganic base is used, a phase transfer catalyst may be added if this increases the conversion.

The intermediates of the formula II are known in many cases or can be prepared by conventional methods, starting from known intermediates (cf. for example EP-A 347 811, EP-A 400 741, EP-A 422 751 and EP-A 409 368).

The sulfones of the general formula III are obtained by oxidizing a corresponding 2-alkylthio-5,6-dihydrofuran[2,3]pyrimidine (cf. Collect. Czech. Chem. Commun. 32 (1967), 1582)

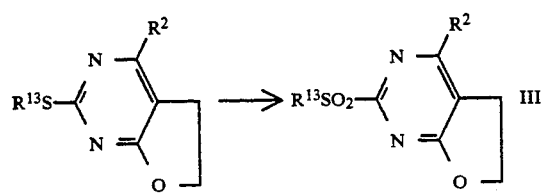

with an oxidizing agent, for example chlorine in water or hydrogen peroxide in glacial acetic acid, under mild conditions.

The preparation of fused pyrimidines is also described, for example, in

Bull Soc. Chim. France (1969), 4344

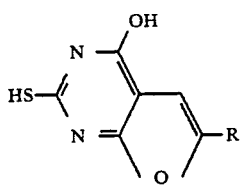

Arch Pharmazie (Weinheim) 331 (1978), 1019

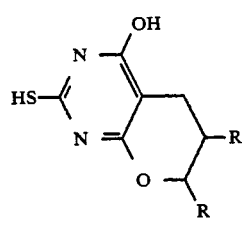

Lipids 21 (1986), 537

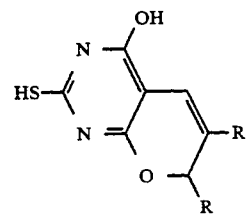

Chem. Ber. 103 (1970), 1250

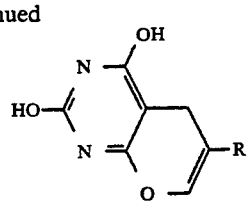

Compounds of the formula I can also be prepared by starting from the corresponding carboxylic acids, i.e. compounds of the formula I in which $R^1$ is hydroxyl, first converting these in a conventional manner into an activated form, such as a halide, an anhydride or an imidazolide, and then reacting this with a corresponding hydroxy compound $HOR^1$. This reaction can be carried out in conventional solvents and often requires the addition of a base, the abovementioned ones being suitable. These two steps may furthermore be simplified, for example, by allowing the carboxylic acid to act on the hydroxy compound in the presence of a water-eliminating agent, such as a carbodiimide.

Compounds of the formula I may also be prepared by starting from the salts of the corresponding carboxylic acids, i.e. from compounds of the formula I in which $R^1$ is OM and M is an alkali metal cation or one equivalent of an alkaline earth metal cation. These salts can be reacted with many compounds of the formula $R^1$—A, where A is a conventional nucleofugic leaving group, for example halogen, such as chlorine, bromine or iodine, or aryl- or alkylsulfonyl which is unsubstituted or substituted by halogen, alkyl or haloalkyl, e.g. toluenesulfonyl or methylsulfonyl, or another equivalent leaving group. Compounds of the formula $R^1$—A having a reactive substituent A are known or can be readily obtained on the basis of general technical knowledge. This reaction can be carried out in the conventional solvents and often requires the addition of a base, the abovementioned ones being suitable.

With regard to the herbicidal activity, preferred compounds I are those in which the substituents have the following meanings:

$R^1$ is hydrogen;

succinylimidoxy;

a 5-membered heteroaromatic structure bonded via a nitrogen atom, such as pyrrolyl, pyrazolyl, imidazolyl or triazolyl, which may carry one or two halogen atoms, in particular fluorine or chlorine, and/or one or two of the following radicals:

alkyl, such as methyl, ethyl, propyl, 1-methylethyl, butyl, 1-methylpropyl, 2-methylpropyl or 1,1-dimethylethyl, preferably methyl, ethyl or 1-methylethyl;

haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl trifluoromethyl, 2,2,2-trifluoroethyl or pentafluoroethyl;

alkoxy as stated above, having from one to four carbon atoms, haloalkoxy, such as difluoromethoxy, trifluoromethoxy, clorodifluoromethoxy, dichlorofluoromethoxy, 1-fluoroethoxy, 2-fluoroethoxy, 2,2-difluoroethoxy, 1,1,2,2,-tetrafluoroethoxy, 2,2,2-trifluoroethoxy, 2-chloro-1,1,2-trifluoroethoxy or pentafluoroethoxy, in particular trifluoromethoxy, and-/or alkylthio, such as methylthio, ethylthio, propylthio, 1-methylethylthio, butylthio, 1-methylpropylthio, 2-methylpropylthio or 1,1-dimethylethylthio, in particular methylthio or ethylthio;

a radical

where m is 0 or 1 and $R^{14}$ and $R^{15}$ may be identical or different and are each hydrogen;

alkyl, in particular methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,2-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl;

alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl, 3-methyl-2-butenyl or 3-methyl-2-pentenyl;

alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentyl, 3-methyl-4-pentynyl, 4-methyl-2-pentylnyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, 2-butynyl, 1-methyl-2-propynyl or 1-methyl-2-butynyl, in particular 2-propynyl;

where these alkyl, alkenyl or alkynyl groups may each carry from one to five halogen atoms, in particular chlorine or fluorine, and/or one or two of the following groups:

$C_1$–$C_6$-alkoxy as stated above, $C_3$–$C_6$-alkenyloxy, $C_3$–$C_6$-alkynyloxy, $C_1$–$C_6$-alkylthio, $C_3$–$C_6$-alkenylthio or $C_3$–$C_6$-alkynylthio, where the alkyl, alkenyl and alkynyl moieties present in these radicals preferably have the meanings stated specifically for $R^1$;

$C_1$–$C_6$-haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy; cyano;

$C_1$–$C_6$-alkylcarbonyl, in particular methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,1,2-trimethylpropylcarbonyl, 1-ethyl-1-methylpropylcarbonyl or 1-ethyl-2-methylpropylcarbonyl;

$C_1$–$C_6$alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-methylbutoxycarbonyl, 1,2-dimethylpropoxycarbonyl, 1,1-dimethylpropoxycarbonyl, 2,2-dimethylpropoxycarbonyl, 1-ethylpropoxycarbonyl, n-hexyloxycarbonyl, 1-methylpentyl-oxycarbonyl, 2-methylpentyloxycarbonyl, 3-methylpentyloxycarbonyl, 4-methylpentyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethylpropoxycarbonyl, 1-ethylbutoxycarbonyl, 2-ethylbutoxycarbonyl, 1-ethyl-2-methylpropoxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentyloxycarbonyl, 2-ethylpentyloxycarbonyl, 1-propylbutoxycarbonyl or octyloxycarbonyl, in particular methoxycarbonyl, ethoxycarbonyl, 1-methylethoxycarbonyl or 1-methylpropoxycarbonyl;

$C_3$–$C_6$-alkenyl, $C_3$–$C_6$-alkynylcarbonyl, $C_3$–$C_6$-alkenyloxycarbonyl or $C_3$–$C_6$-alkynyloxycarbonyl, where the alkenyl or alkynyl radicals are preferably defined as stated specifically above;

bis-$C_1$–$C_6$-dialkylamino, in particular dimethylamino, diethylamino, dipropylamino, N-propyl-N-methylamino, N-propyl-N-ethylamino, diisopropylamino, N-isopropyl-N-methylamino, N-isopropyl-N-ethylamino, N-isopropyl-N-propylamino;

cyclo-C–C$_6$-alkyl, such as cyclopropyl, cyclobutyl, cyclopentyl or cyclohexyl;

unsubstituted or substituted phenyl, in particular phenyl, 2-chlorophenyl, 3-chlorophenyl, 4-chlorophenyl, 2-fluorophenyl, 3-fluorophenyl, 4-fluorophenyl, 2-methylphenyl, 3-methylphenyl, 4-methylphenyl, 2-trifluoromethylphenyl, 3-trifluoromethylphenyl, 4-trifluoromethylphenyl, 4-methoxyphenyl, 3-methoxyphenyl or 2-methoxyphenyl;

unsubstituted or substituted cyclo-C$_3$–C$_6$-alkyl as stated specifically above, for example 1-methylthiocyclopropyl, 1-methylcyclohexyl, 1-methylcyclopropyl or 1-methoxycyclohexyl, or R$^{14}$ together with R$^{15}$ form an unsubstituted or substituted, cyclized C$_4$–C$_7$-alkylene chain or together form an unsubstituted or substituted, cyclized C$_3$–C$_6$-alkylene chain having a hetero atom selected from the group consisting of oxygen, sulfur and nitrogen, such as —(CH$_2$)$_4$—, —(CH$_2$)$_5$—, —(CH$_2$)$_6$—, —(CH$_2$)$_7$—, —(CH$_2$)$_2$—O—(CH$_2$)$_2$—, —CH$_2$—O(CH$_2$)$_3$—, —(CH$_2$)$_2$—S—(CH$_2$)$_2$—, —CH$_2$—S—(CH$_2$)—CH$_2$—O— (CH$_2$)$_2$—, —CH$_2$—S—(CH$_2$)$_2$—, —(CH$_2$)$_2$—NH—(CH$_2$)$_2$—, —(CH$_2$)$_2$—N(CH$_3$)—(CH$_2$)—;

R$^1$ is furthermore a group

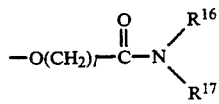

where R$^{16}$ and R$^{17}$ are identical or different and are each hydrogen, C$_1$–C$_6$-alkyl, C$_3$–C$_6$-alkenyl or C$_3$–C$_6$-alkynyl, each as stated above for R$^{14}$/R$^{15}$, or unsubstituted or substituted phenyl and l is 1, 2, 3 or 4;

R$^1$ is furthermore a group

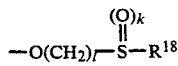

where R$^{18}$ is C$_1$–C$_6$-alkyl, unsubstituted or substituted phenyl, C$_1$–C$_6$-haloalkyl, C$_3$–C$_6$-alkenyl or C$_3$–C$_6$-alkynyl, each as stated specifically above for R$^{14}$/R$^{15}$, l is 1, 2, 3 or 4 and k is 0, 1 or 2;

R$^1$ is furthermore OR$^5$, where R$^5$ may be:

hydrogen, the cation of an alkali metal or the cation of an alkaline earth metal, such as lithium, sodium, potassium, calcium, magnesium or barium, or an environmentally compatible organic ammonium ion or ammonium [NH$_4$⊕]; C$_3$–C$_{12}$-cycloalkyl, in particular C$_3$–C$_6$-cycloalkyl, such as cyclopropyl, cyclobutyl, cyclopentyl or cyclohexyl, which is unsubstituted or substituted by from one to three C$_1$–C$_4$-alkyl radicals;

C$_1$–C$_{10}$-alkyl, in particular methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,2-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, n-heptyl, 1-methylhexyl, 2-methylhexyl, 3-methylhexyl, 4-methylhexyl, 5-methylhexyl, 1-ethylpentyl, 2ethylpentyl, 1-propylbutyl or octyl, which may carry from one to five of the abovementioned halogen atoms, in particular fluorine and chlorine, and/or one of the following radicals:

C$_1$–C$_4$-alkoxy, C$_1$–C$_4$-alkylthio, cyano, C$_1$–C$_8$-alkylcarbonyl, C$_3$–C$_{12}$-cycloalkyl, C$_1$–C$_8$-alkoxycarbonyl, phenyl, phenoxy or phenylcarbonyl, where the aromatic radicals in turn may each carry from one to five halogen atoms and/or from one to three of the following radicals: C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio;

C$_1$–C$_{10}$alkyl as stated above for R$^5$, which may carry from one to five halogen atoms, in particular fluorine and/or chlorine, and carries one of the following radicals: a 5-membered heteroaromatic structure containing from one to three nitrogen atoms or a 5-membered heteroaromatic structure containing one nitrogen atom and one oxygen or sulfur atom, which may carry from one to four halogen atoms and/or one or two of the following radicals: C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio, particular examples being 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropylisoxazol-5-yl, 3-methylisoxazol-5-yl, oxazol-2-yl, thiazol-2-yl, imidazol-2-yl, 3-ethylisoxazol-5-yl, 3-phenylisoxazol-5-yl or 3tert-butylisoxazol-5-yl;

C$_2$–C$_6$-alkyl which carries one of the following radicals in the 2-position: C$_1$–C$_6$-alkoximino, C$_3$–C$_6$-alkynyloximino, C$_3$–C$_6$-haloalkenyloximino or benzyloximino;

C$_3$–C$_6$alkenyl or C$_3$–C$_6$-alkynyl, where these groups in turn may carry from one to five halogen atoms;

phenyl which may carry from one to five halogen atoms and/or from one to three of the following radicals: C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio;

a 5-membered heteroaromatic structure which is bonded via a nitrogen atom, contains from one to three nitrogen atoms and may carry one or two halogen atoms and/or one or two of the following radicals: C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio, particular examples being 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl or 3,4-dichloroimidazol-1-yl;

a group —N=CR$^6$R$^7$, where R$^6$ and R$^7$ are each straight-chain or branched C$_1$–C$_{20}$-alkyl, preferably C$_1$–C$_{15}$-alkyl, in particular C$_1$–C$_9$-alkyl, which may carry a phenyl, a C$_1$–C$_4$-alkoxy and/or a C$_1$–C$_4$-alkythio radical, or are each phenyl, or together form C$_3$–C$_{12}$-alkylene, preferably C$_4$–C$_7$-alkylene, which may carry from one to three C$_1$–C$_3$-alkyl groups, preferably methyl or ethyl;

R$^1$ is furthermore a radical

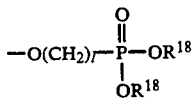

where $R^{18}$ and l have the abovementioned meanings, or $R^1$ is a radical

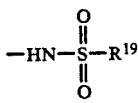

where $R^{19}$ is $C_1-C_6$-alkyl or phenyl, which in turn may carry from one to four of the following substituents: halogen, nitro, cyano or $C_1-C_6$-alkyl;

$R^2$ is halogen, such as fluorine, chlorine or bromine, in particular fluorine or chlorine, $C_1-C_4$-alkyl, $C_1-C_4$-haloalkyl, $C_1-C_4$-alkoxy, $C_1-C_4$-haloalkoxy or $C_1-C_4$-alkylthio as stated specifically above for $R^{14}/R^{15}$;

$R^3$ is hydrogen;

$C_1-C_8$-alkyl, $C_1-C_8$-alkenyl, $C_1-C_8$-alkynyl, phenyl, $C_3-C_8$-cycloalkenyl or $C_3-C_8$-cycloalkyl, each of which may carry up to five halogen atoms and, independently of one another, up to three of the following substituents: hydroxyl, $C_1-C_4$-haloalkyl, $C_1-C_4$-alkoxy, $C_1-C_4$-alkylthio, cyano, nitro, $C_1-C_4$-alkoxycarbonyl, $C_1-C_4$-alkylcarbonyl, $C_1-C_4$-alkyl, phenylcarbonyl, $C_3-C_{12}$-cycloalkyl or $C_3-C_{12}$-cycloalkenyl;

a 5-membered heterocyclic structure containing no double bonds or one or two double bonds and from one to four nitrogen atoms or one or two nitrogen atoms and in addition one sulfur or oxygen atom, which may carry from one to three halogen atoms and/or from one to three of the following radicals: nitro, cyano, $C_1-C_4$-alkyl, $C_1-C_4$-alkoxy, $C_1-C_4$-alkylthio, $C_1-C_4$-haloalkyl or phenyl, which in turn may carry from one to three halogen atoms and/or from one to three methyl groups, for example 3-isopropylisoxazol-5-yl, 3-methylisoxazol-5-yl, oxazol-2-yl, thiazol-2-yl, imidazol-2-yl, 3-phenylisoxazol-5-yl, 3-tert-butylisoxazol-5-yl, 3-isopropylisoxazolin-5-yl, 3-ethylisoxazolin-5-yl, 3-phenylisoxazolin-5yl, 3-tert-butylisoxazolin-5-yl, 4-phenylthiazol-2-yl, 4-phenyloxazol-2-yl, 4,5-dimethylthiazol-2-yl, 4,5-dimethyloxazol-2-yl, 3-methyl-4-phenylthiazol-2-yl, 4-methyl-3-phenylthiazol-2-yl, 3-methyl-4-phenyloxazol-2-yl, 4-methyl-3-phenyloxazol-2-yl, 5-phenyl-[1,3,4]oxadiazol-2-yl, 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 1-imidazolyl or [1,2,4]triazol-1-yl;

thienyl which may carry from one to three halogen atoms and/or from one to three of the following radicals: $C_1-C_4$-alkyl, $C_1$- or $C_2$-haloalkyl or nitro;

pyridyl which may carry from one to three halogen atoms and/or from one to three of the following radicals: $C_1-C_4$-alkyl, $C_1$- or $C_2$-haloalkyl or nitro;

naphthyl, quinolyl, benzoxazolyl, benzothiazolyl, benzothienyl, indazolyl or benzotriazolyl, each of which may carry from one to three halogen atoms and/or from one to three of the following radicals: $C_1-C_4$-alkyl or $C_1$- or $C_2$-haloalkyl;

phenyl which in turn may carry from one to five halogen atoms and/or from one to three of the following radicals: $C_1-C_4$-alkyl, $C_1-C_4$-alkoxy, $C_1-C_4$-haloalkyl, $C_1-C_4$-haloalkoxy, cyano, nitro, $C_1-C_4$-dialkylamino and/or $C_1-C_4$-alkylthio;

a 5-membered or 6-membered heterocyclic structure containing no double bonds or one or two double bonds and one or two oxygen or sulfur atoms, which may furthermore carry the following radicals: $C_1-C_4$-alkyl, $C_1-C_4$-alkoxy, $C_1-C_4$-haloalkyl or $C_1-C_4$-haloalkoxy, for example tetrahydropyran-4-yl, tetrahydrothiopyran-3-yl, tetrahydropyran-3-yl, [2,6]dithiacyclohexyl, [2,5]dithiacyclopentyl, [2,6]dioxacyclohexyl, [2,5]dioxacyclopentyl, 1-methyl-[2,6]dithiacyclohexyl or dihydropyran-3-yl; $R^3$ is a 5-membered or 6-membered heterocyclic structure containing no double bonds or one or two double bonds and from one to four nitrogen atoms or one or two nitrogen atoms and in addition one sulfur or oxygen atom, which may carry from one to three halogen atoms and/or from one to three of the following radicals: nitro, cyano, $C_1-C_4$-alkyl, $C_1-C_4$-alkylthio, $C_1-C_4$-haloalkyl, $C_1-C_4$-haloalkoxy, $C_1-C_4$-alkoxy or phenyl, which in turn may carry from one to three halogen atoms and/or from one to three methyl groups, examples being the following heterocyclic structures: 3-isopropylisoxazol-5-yl, 3-methylisoxazol-5-yl, oxazol-2-yl, thiazol-2-yl, imidazol-2-yl, 3-ethylisoxazol-5-yl, 3-phenylisoxazol-5yl, 3-tert-butylisoxazol-5-yl, 3-isopropylisoxazolin-5-yl, 3-ethylisoxazolin-5-yl, 3-phenylisoxazolin-5-yl, 3-tert-butylisoxazolin-5-yl, 4-phenylthiazol-2-yl, 4-phenyloxazol-2-yl, 4,5-dimethylthiazol-2-yl, 4,5-dimethyloxazol-2-yl, 3-methyl-4-phenylthiazol-2-yl, 4-methyl-3-phenylthiazol-2-yl, 3-methyl-4-phenyloxazol-2-yl, 4-methyl-3-phenyloxazol-2-yl, 5-phenyl[1,3,4]oxadiazol-2-yl, 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 1-imidazolyl, [1,2,4[triazol-1-yl, morpholin-1-yl, 3,5-dimethylmorpholin-1-yl or 1-piperidyl;

pyridyl which may carry from one to three halogen atoms and/or from one to three of the following radicals: $C_1-C_4$-alkyl, $C_1$- or $C_2$-haloalkyl and nitro; naphthyl, quinolyl, benzoxazolyl, indazolyl or benzotriazolyl, each of which may carry from one to three halogen atoms and/or from one to three of the following radicals: $C_1-C_4$-alkyl and $C_1$ or $C_2$-haloalkyl;

a 5-membered or 6-membered heterocyclic structure containing no double bonds or one or two double bonds and one or two oxygen or sulfur atoms, such as tetrahydropyran-4-yl, tetrahydrothiopyran-3-yl, tetrahydropyran-3-yl, [2,6]dithiacyclohexyl, [2,5]dithiacyclopentyl, [2,6]dioxacyclohexyl, [2,5]dioxacyclopentyl, 1-methyl[2,6]dithiacyclohexyl or dihydropyran-3-yl, where the heterocyclic structure may furthermore carry the following radicals: halogen, nitro, $C_1-C_4$-alkyl, $C_1-C_4$-alkoxy, $C_1-C_4$-haloalkyl or $C_1-C_4$-haloalkoxy;

$R^3$ together with $R^1$ are an unsubstituted or substituted $C_4-C_7$-alkylene chain, where $CH_2$ may be replaced by oxygen, sulfur or nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—O$(CH_2)_3$—, —$(CH_2)_2$—S—$(CH_2)_2$—, —$CH_2$—S—$(CH_2)_3$—, —$CH_2$—O—$(CH_2)_2$—, —$CH_2$—S—$(CH_2)_2$—, —$(CH_2)_2$—N-

H—(CH$_2$)$_2$—, —(CH$_2$)$_2$—N(CH$_3$)—(CH$_2$)—; X is oxygen, sulfur or a single bond, in the last-mentioned case the CH(R$^3$) radical being bonded directly to the pyrimidyl radical; and Y is a C$_2$-C$_4$-alkylene or C$_2$—C$_4$-alkenylene chain in which in each case a methylene group may be substituted by an oxo group, e.g. —CH$_2$—CH$_2$—, —(CH$_2$)$_3$—, —(CH$_2$)$_4$—, —CH=CH—, —CH$_2$—CO—, —CO—CH$_2$—, —CH$_2$—CH$_2$—CO—, —CH=CH—CO— or where the alkylene or alkenylene chain may be substituted by C$_1$-C$_4$-alkyl, phenyl, C$_1$-C$_4$-alkoxy or C$_1$-C$_4$-alkoxycarbonyl.

The user of the expression unsubstituted or substituted means in each case that the groups so referred to may carry one or more, for example from one to three, of the following substituents: halogen, nitro, cyano, C$_1$-C$_6$-alkyl, C$_1$-C$_6$-haloalkyl, C$_1$-C$_6$-alkoxy or C$_1$-C$_6$-alkylthio.

Suitable salts of the compounds I are agriculturally useful salts, for example alkali metal salts, in particular the potassium or sodium salt, alkaline earth metal salts, in particular the calcium, magnesium or barium salt, manganese, copper, zinc or iron salts and ammonium, phosphonium, tetraalkylammonium, benzyltrialkylammonium, trialkylsulfonium or trialkylsulfoxonium salts.

Particularly preferred compounds of the formula I are those in which R$^2$ is methoxy or ethoxy, X is oxygen and Y is ethylene and the remaining radicals have the abovementioned meanings.

Furthermore, lactic acid derivatives of the formula I where R$^1$ is OR$^5$, R$^5$ is hydrogen, C$_1$-C$_{10}$-alkyl, benzyl, C$_3$-C$_6$-alkenyl or C$_3$-C$_6$-alkynyl, R$^2$ is methoxy, R$^3$ is hydrogen or C$_1$-C$_8$-alkyl which may be substituted as stated in claim 1, X is oxygen or sulfur and Y is a C$_2$H$_4$ chain are particularly preferred.

Other particularly preferred lactic acid derivatives of the formula I are those in which R$^1$ is OR$^5$, R$^5$ is a group —N=CR$^6$R$^7$, where R$^6$ and R$^7$ are each C$_1$-C$_4$-alkyl which is unsubstituted or substituted by phenyl, C$_1$-C$_4$-alkoxy and/or C$_1$-C$_4$-alkylthio, or are each phenyl, or R$^6$ together with R$^7$ forms a C$_3$-C$_6$-alkylene chain which may be substituted by C$_1$-C$_3$-alkyl, R$^2$ is methoxy, R$^3$ is hydrogen or C$_1$-C$_8$-alkyl which may be substituted as stated in claim 1, X is oxygen or sulfur and Y is a C$_2$H$_4$ chain.

Examples of preferred compounds are shown in the Table below:

TABLE

| R$^1$ | R$^3$ | R$^2$ | X |
|---|---|---|---|
| OH | Methyl | OCH$_3$ | O |
| OH | Ethyl | OCH$_3$ | O |
| OH | n-Propyl | OCH$_3$ | O |
| OH | i-Propyl | OCH$_3$ | O |
| OH | t-Butyl | OCH$_3$ | O |
| OH | n-Butyl | OCH$_3$ | O |
| OH | i-Butyl | OCH$_3$ | O |
| OH | Cyclopropyl | OCH$_3$ | O |
| OH | Cyclobutyl | OCH$_3$ | O |
| OH | Cyclopentyl | OCH$_3$ | O |
| OH | Cyclohexyl | OCH$_3$ | O |
| OH | 1-Methylthiocyclopropyl | OCH$_3$ | O |
| OH | 2-Fluoro-2-propyl | OCH$_3$ | O |
| OH | 2-Phenyl-2-propyl | OCH$_3$ | O |
| OH | Phenyl | OCH$_3$ | O |
| OH | 1-Phenyl-1-ethyl | OCH$_3$ | O |
| OH | 2-Thienyl-2-propyl | OCH$_3$ | O |
| OH | 1-Naphthyl-1-ethyl | OCH$_3$ | O |
| OH | sec.-Butyl | OCH$_3$ | O |
| OH | Methyl | OCH$_3$ | S |
| OH | Ethyl | OCH$_3$ | S |
| OH | n-Propyl | OCH$_3$ | S |
| OH | i-Propyl | OCH$_3$ | S |
| OH | t-Butyl | OCH$_3$ | S |
| OH | n-Butyl | OCH$_3$ | S |
| OH | i-Butyl | OCH$_3$ | S |
| OH | Cyclopropyl | OCH$_3$ | S |
| OH | Cyclobutyl | OCH$_3$ | S |
| OH | Cyclopentyl | OCH$_3$ | S |
| OH | Cyclohexyl | OCH$_3$ | S |
| OH | 1-Methylthiocyclopropyl | OCH$_3$ | S |
| OH | 2-Fluoro-2-propyl | OCH$_3$ | S |
| OH | 2-Phenyl-2-propyl | OCH$_3$ | S |
| OH | Phenyl | OCH$_3$ | S |
| OH | 1-Phenyl-1-ethyl | OCH$_3$ | S |
| OH | 2-Thienyl-2-propyl | OCH$_3$ | S |
| OH | 1-Naphthyl-1-ethyl | OCH$_3$ | S |
| OH | sec.-Butyl | OCH$_3$ | S |
| OCH$_3$ | Methyl | OCH$_3$ | O |
| OCH$_2$CH=CH$_2$ | Ethyl | OCH$_3$ | O |
| OCH$_2$CH=CH$_2$ | n-Propyl | OCH$_3$ | O |
| OCH$_2$CH=CH$_2$ | i-Propyl | OCH$_3$ | O |
| Propargyloxy | i-Propyl | OCH$_3$ | O |
| H | i-Propyl | OCH$_3$ | O |
| OCH$_2$CH=CH$_2$ | t-Butyl | OCH$_3$ | O |
| trans-3-Chloro-2-propen-1-yloxy | n-Butyl | OCH$_3$ | O |
| OCH$_2$CH=CH$_2$ | i-Butyl | OCH$_3$ | O |
| OCH$_2$CH=CH$_2$ | Cyclopropyl | OCH$_3$ | O |
| OCH$_2$CH=CH$_2$ | Cyclobutyl | OCH$_3$ | O |
| OCH$_2$CH=CH$_2$ | Cyclopentyl | OCH$_3$ | O |
| OCH$_2$CH=CH$_2$ | Cyclohexyl | OCH$_3$ | O |
| OCH$_2$CH=CH$_2$ | 1-Methylthiocyclopropyl | OCH$_3$ | O |
| OCH$_2$CH=CH$_2$ | 2-Fluoro-2-propyl | OCH$_3$ | O |
| OCH$_2$CH=CH$_2$ | 2-Phenyl-2-propyl | OCH$_3$ | O |
| OCH$_2$CH=CH$_2$ | Phenyl | OCH$_3$ | O |
| OCH$_2$CH=CH$_2$ | 1-Phenyl-1-ethyl | OCH$_3$ | O |
| OCH$_2$CH=CH$_2$ | 2-Thienyl-2-propyl | OCH$_3$ | O |
| OCH$_2$CH=CH$_2$ | 1-Naphthyl-1-ethyl | OCH$_3$ | O |
| OCH$_2$CH=CH$_2$ | sec.-Butyl | OCH$_3$ | O |
| Cyclohexyloxy | Methyl | OCH$_3$ | O |
| 2-Ethoxyimino-1-ethoxy | Ethyl | OCH$_3$ | O |
| 2-Methoxyimino-1-ethoxy | n-Propyl | OCH$_3$ | O |
| 2-Allyloxyimino-1-ethoxy | i-Propyl | OCH$_3$ | O |
| 2-Allyloxyimino-1-propoxy | i-Propyl | OCH$_3$ | O |
| 2-Benzyloxyimino-1-ethoxy | i-Propyl | OCH$_3$ | O |
| 2-Allyloxyimino-1-ethoxy | t-Butyl | OCH$_3$ | O |
| 2-Allyloxyimino-1-ethoxy | n-Butyl | OCH$_3$ | O |
| 2-Allyloxyimino-1-propoxy | i-Butyl | OCH$_3$ | O |
| 2-Allyloxyimino-1-ethoxy | Cyclopropyl | OCH$_3$ | O |
| 2-Allyloxyimino-1-ethoxy | Cyclobutyl | OCH$_3$ | O |
| 2-Allyloxyimino-1-ethoxy | Cyclopentyl | OCH$_3$ | O |

TABLE-continued

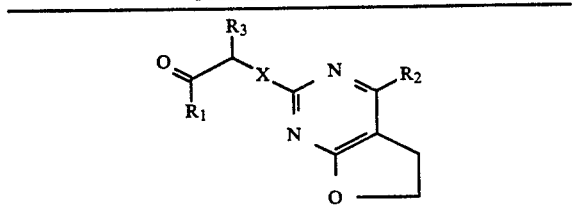

| R¹ | R³ | R² | X |
|---|---|---|---|
| 2-Allyloxyimino-1-ethoxy | Cyclohexyl | OCH₃ | O |
| 2-Allyloxyimino-1-ethoxy | 1-Methylthiocyclopropyl | OCH₃ | O |
| 2-Allyloxyimino-1-ethoxy | 2-Fluoro-2-propyl | OCH₃ | O |
| 2-Allyloxyimino-1-ethoxy | 2-Phenyl-2-propyl | OCH₃ | O |
| 2-Allyloxyimino-1-ethoxy | Phenyl | OCH₃ | O |
| 2-Allyloxyimino-1-ethoxy | 1-Phenyl-1-ethyl | OCH₃ | O |
| 2-Allyloxyimino-1-ethoxy | 2-Thienyl-2-propyl | OCH₃ | O |
| 2-Allyloxyimino-1-ethoxy | 1-Naphthyl-1-ethyl | OCH₃ | O |
| 2-Allyloxyimino-1-ethoxy | sec.-Butyl | OCH₃ | O |
| 2-Propaniminoxy | i-Propyl | OCH₃ | O |
| 1-Phenyl-1-ethaniminoxy | i-Propyl | OCH₃ | O |
| Cyclohexaniminoxy | i-Propyl | OCH₃ | O |
| Benzyloxy | i-Propyl | OCH₃ | O |
| 4-Chlorobenzyloxy | i-Propyl | OCH₃ | O |
| Methylthiomethoxy | i-Propyl | OCH₃ | O |
| Ethoxycarbonyl-methoxy | i-Propyl | OCH₃ | O |
| 1-Imidazolyl | i-Propyl | OCH₃ | O |
| 1-Pyrazolyloxy | i-Propyl | OCH₃ | O |
| N,N-Dimethylaminoxy | i-Propyl | OCH₃ | O |
| 2-Chloroethoxy | i-Propyl | OCH₃ | O |
| 2-Methylsulfonyl-ethoxy | i-Propyl | OCH₃ | O |
| 1-Piperidinyloxy | i-Propyl | OCH₃ | O |
| Succinylimidoxy | i-Propyl | OCH₃ | O |
| Methylsulfonamido | i-Propyl | OCH₃ | O |
| OH | 2-Methyl-3-buten-2-yl | OCH₃ | O |
| OH | E-1-Chloro-3-methyl-1-buten-3-yl | OCH₃ | O |
| OH | 3-Buten-2-yl | OCH₃ | O |
| OH | 1-Cyclopentyl-1-ethyl | OCH₃ | O |
| OH | 1-Cyclopentyl-1-ethyl | OCH₃ | O |
| OH | Tetrahydropyran-4-yl | OCH₃ | O |
| OH | Tetrahydrothiopyran-3-yl | OCH₃ | O |
| OH | Tetrahydropyran-3-yl | OCH₃ | O |
| OH | 3-Isopropylisoxazolin-5-yl | OCH₃ | O |
| OH | 2-Methyl-3-butyn-2-yl | OCH₃ | O |
| OH | 3-Butyn-2-yl | OCH₃ | O |
| OH | 1-(3'-Isopropyl-isoxazolin-5'-yl)-1-ethyl | OCH₃ | O |
| OH | 1-(Tetrahydropyran-3'-yl)-1-ethyl | OCH₃ | O |
| OH | Cyclopentylmethyl | OCH₃ | O |
| OH | Cyclopropylmethyl | OCH₃ | O |
| OH | 1-Cyclopropyl-1-ethyl | OCH₃ | O |
| OH | 1-Cyclopentyl-1-ethyl | OCH₃ | O |
| OH | 2-(4'-Methylphenyl)-2-propyl | OCH₃ | O |
| OH | 2-(3'-Trifluoromethyl-phenyl)-2-propyl | OCH₃ | O |
| OH | 2-(4'-Chlorophenyl)-2-propyl | OCH₃ | O |
| OH | 1-(2'-Methoxyphenyl)-1-ethyl | OCH₃ | O |
| OH | 2,6-Dimethylbenzyl | OCH₃ | O |
| OH | 1-(2',6'Dimethyl-phenyl)-1-ethyl | OCH₃ | O |
| OH | 2-(Thiazol-2'-yl)-2-propyl | OCH₃ | O |
| OH | 1-(4'-Phenylthiazol-2'-yl)-ethyl | OCH₃ | O |
| OH | 2-Methyl-3-buten-2-yl | OCH₃ | S |
| OH | E-1-Chloro-3-methyl-1-buten-3-yl | OCH₃ | S |

TABLE-continued

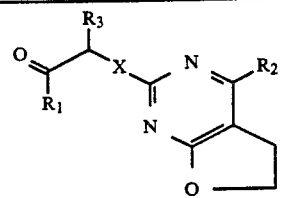

| R¹ | R³ | R² | X |
|---|---|---|---|
| OH | 3-Buten-2-yl | OCH₃ | S |
| OH | 1-Cyclopentyl-1-ethyl | OCH₃ | S |
| OH | 1-Cyclopropyl-1-ethyl | OCH₃ | S |
| OH | Tetrahydropyran-4-yl | OCH₃ | S |
| OH | Tetrahydrothiopyran-3-yl | OCH₃ | S |
| OH | Tetrahydropyran-3-yl | OCH₃ | S |
| OH | 3-Isopropylisoxazolin-5-yl | OCH₃ | S |
| OH | 2-Methyl-3-butyn-2-yl | OCH₃ | S |
| OH | 3-Butyn-2-yl | OCH₃ | S |
| OH | 1-(3'-Isopropyl-isoxazolin-5'-yl)-1-ethyl | OCH₃ | S |
| OH | 1-(Tetrahydropyran-3'-yl)-1-ethyl | OCH₃ | S |
| OH | Cyclopentylmethyl | OCH₃ | S |
| OH | Cyclopropylmethyl | OCH₃ | S |
| OH | 1-Cyclopropyl-1-ethyl | OCH₃ | S |
| OH | 1-Cyclopentyl-1-ethyl | OCH₃ | S |
| OH | 2-(4'-Methylphenyl)-2-propyl | OCH₃ | S |
| OH | 2-(3'-Trifluoromethyl-phenyl)-2-propyl | OCH₃ | S |
| OH | 2-(4'-Chlorophenyl)-2-propyl | OCH₃ | S |
| OH | 1-(2'-Methoxyphenyl)-1-ethyl | OCH₃ | S |
| OH | 2,6-Dimethylbenzyl | OCH₃ | S |
| OH | 1-(2',6'-Dimethyl-phenyl)-1-ethyl | OCH₃ | S |
| OH | 2-(Thiazol-2'-yl)-2-propyl | OCH₃ | S |
| OH | 1-(4'-Phenylthiazol-2'-yl)-1-ethyl | OCH₃ | S |
| Ethoxy | 3-Buten-2-yl | OCH₃ | S |
| Ethoxy | 1-Cyclopentyl-1-ethyl | OCH₃ | S |
| Ethoxy | 1-Cyclopropyl-1-ethyl | OCH₃ | S |
| Ethoxy | Tetrahydropyran-4-yl | OCH₃ | S |
| Ethoxy | Tetrahydrothiopyran-3-yl | OCH₃ | S |
| Ethoxy | Tetrahydropyran-3-yl | OCH₃ | S |
| Ethoxy | 3-Isopropylisoxazolin-5-yl | OCH₃ | S |
| Ethoxy | 2-Methyl-3-butyn-2-yl | OCH₃ | S |
| Ethoxy | 3-Butyn-2-yl | OCH₃ | S |
| Ethoxy | 1-(3'-Isopropyl-isoxazolin-5'-yl)-1-ethyl | OCH₃ | S |
| Ethoxy | 1-(Tetrahydropyran-3'-yl)-1-ethyl | OCH₃ | S |
| Ethoxy | Cyclopentylmethyl | OCH₃ | S |
| Ethoxy | Cyclopropylmethyl | OCH₃ | S |
| Ethoxy | 1-Cyclopropyl-1-ethyl | OCH₃ | S |
| Ethoxy | 1-Cyclopentyl-1-ethyl | OCH₃ | S |
| Ethoxy | 2-(4'-Methylphenyl)-2-propyl | OCH₃ | S |
| Ethoxy | 2-(3'-Trifluoromethyl-phenyl)-2-propyl | OCH₃ | S |
| Ethoxy | 2-(4'-Chlorophenyl)-2-propyl | OCH₃ | S |
| Ethoxy | 1-(2'Methoxyphenyl)-1-ethyl | OCH₃ | S |
| Ethoxy | 2,6-Dimethylbenzyl | OCH₃ | S |
| Ethoxy | 1(2',6'-Dimethyl-phenyl)-1-ethyl | OCH₃ | S |
| Ethoxy | 2-(Thiazol-2'-yl)-2-propyl | OCH₃ | S |
| Ethoxy | 1-(4'-Phenylthiazol-2'-yl)-1-ethyl | OCH₃ | S |
| Ethoxy | 3-Buten-2-yl | OCH₃ | O |
| Ethoxy | 1-Cyclopentyl-1-ethyl | OCH₃ | O |
| Ethoxy | 1-Cyclopropyl-1-1ethyl | OCH₃ | O |
| Ethoxy | Tetrahydropyran-4-yl | OCH₃ | O |
| Ethoxy | Tetrahydrothiopyran-3-yl | OCH₃ | O |
| Ethoxy | Tetrahydropyran-3-yl | OCH₃ | O |
| Ethoxy | 3-Isopropylisoxazolin-5-yl | OCH₃ | O |
| Ethoxy | 2-Methyl-3-butyn-2-yl | OCH₃ | O |
| Ethoxy | 3-Butyn-2-yl | OCH₃ | O |
| Ethoxy | 1-(3'-Isopropyl-isoxazolin-5'-yl)-1-ethyl | OCH₃ | O |
| Ethoxy | 1-(Tetrahydropyran-3'-yl)-1-ethyl | OCH₃ | O |
| Ethoxy | Cyclopentylmethyl | OCH₃ | O |
| Ethoxy | Cyclopropylmethyl | OCH₃ | O |

TABLE-continued

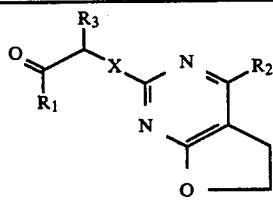

| R¹ | R³ | R² | X | |
|---|---|---|---|---|
| Ethoxy | 1-Cyclopropyl-1-ethyl | OCH₃ | O | |
| Ethoxy | 1-Cyclopentyl-1-ethyl | OCH₃ | O | |
| Ethoxy | 2-(4'-Methylphenyl)-2-propyl | OCH₃ | O | |
| Ethoxy | 2-(3'-Trifluoromethyl-phenyl)-2-propyl | OCH₃ | O | |
| OH | 2(4'-Chlorophenyl)-2-propyl | OCH₃ | O | |
| OH | 1-(2'-Methoxyphenyl)-1-ethyl | OCH₃ | O | |
| OH | 2,6-Dimethylbenzyl | OCH₃ | O | |
| OH | 1-(2',6'-Dimethylphenyl)-1-ethyl | OCH₃ | O | |
| OH | 2(Thiazol-2'-yl)-2-propyl | OCH₃ | O | |
| OH | 1-(4'-Phenylthiazol-2'-yl)-1-ethyl | OCH₃ | O | |
| OH | i-Propyl | OC₂H₅ | O | |

The compounds I, or herbicidal agents containing them, may be applied for instance in the form of directly sprayable solutions, powders, suspension (including high-percentage aqueous, oily or other suspension), dispersion, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc. The formulations contain from 0.01 to 95, and preferably 0.5 to 90, % by weight of active ingredient. The active ingredients are used in a purity of 90 to 100, and preferably 95 to 100, % (according to the NMR spectrum).

The compounds I according to the invention may be formulated for example as follows:

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 5 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion in obtained containing 0.02% by weight of the active ingredient.

IV. 20 parts by weight of compound no. 5 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having goof adherence.

VIII. 20 parts by weight of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.01 to 1, kg of active ingredient per hectare.

In view of the numerous application methods possible, the compounds according to the invention or agents containing them may be used in a large number of crops. Those which follow are given by way of example:

| | |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Petroselinum crispum spp. tuberosum | parsley |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Triofolium pratense | red clover |
| Triticum aestivum | wheat |
| Triticum durum | wheat |
| Vicia faba | tick beans |
| Vitis vinifera | grapes |
| Zea mays | Indian corn, sweet corn, maize |

To increase the spectrum of action and to achieve synergistic effects, the compounds I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the novel compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Synthesis Examples

EXAMPLE 1

Manufacture of 2-methylsulfonyl-4-methoxy-5,6-dihydrofuran[2,3-d]pyrimidine

2-Methylthio-4-chloro-5,6-dihydrofuran[2,3-d]pyrimidine

At 125°–130° C., 212.0 g (1.07 mol) of trichloromethyl chloroformate is dripped over a 3-hour period into a suspension of 65.8 g (0.357 mol) of 2-methylthio-4-hydroxy-5,6-dihydrofuran[2,3-d]pyrimidine (Collect. Czech. Chem. Commun. 32, 1582 (1967)) in 900 ml of chlorobenzene, 0.5 ml of DMF being added three times. After the reaction mixture has been stirred for 1 hour at 130° C., it is evaporated down under reduced pressure and the residue (74 g of an oil) is chromatographed on silica gel (9:1 mixture of toluene and cyclohexane). Yield: 17.0 g of the abovementioned product of melting point 68°–71° C.

2-Methylthio-4-methoxy-5,6-dihydrofuran[2,3-d]pyrimidine 17.0 g (84 mmol) of 2-methylthio-4-chloro-5,6-dihydrofuran[2,3-d]pyrimidine is introduced into 90 ml of methanol, 21.1 g (0.117 mol) of 30% strength sodium methylate solution is dripped in at 45° C., and the whole is stirred for 2 hours at 50° C. After the reaction mixture has been neutralized to pH 6 with a small amount of glacial acetic acid, it is stirred into 350 ml of ice water. Suction filtration, washing with water and drying give 15.1 g of the abovementioned product of melting point 90°–92° C.

2-Methylsulfonyl-4-methoxy-5,6-dihydrofuran[2,3-d]pyrimidine

AT 0 to 5° C. and while stirring, chlorine is passed into a mixture of 15.1 g (76 mmol) of 2-methylthio-4-methoxy-5,6-dihydro-furan[2,3-d]pyrimidine in 120 ml of methylene chloride and 76 ml of water until the reaction mixture turns pale yellow. After stirring for a further 30 minutes, the organic phase is separated off and the aqueous phase is extracted with 100 ml of methylene chloride. The combined organic phases are dried and evaporated down. After chromatography on silica gel (4:1 mixture of toluene and ethyl acetate) there is obtained from the residue (16.7 g) 5.5 g of the abovementioned produce of melting point 122°–124° C.

EXAMPLE 2

Manufacture of 2-methylsulfonyl-4-methyl-5,6-dihydrofuran[2,3-d]pyrimidine

Similarly to Example 1, the abovementioned product is obtained from 2-methylthio-4-methyl-5,6-dihydrofuran[2,3-d]pyrimidine (Collect. Czech. Chem. Commun. 32, 1582 (1967); m.p. 85°–90° C. in a yield of 80%.

The sulfones III listed in Table 2 may be obtained correspondingly.

TABLE

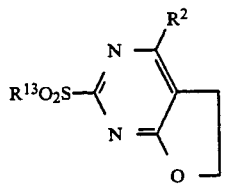

| R13 | R2 |
|---|---|
| CH3 | Cl |
| CH3 | OCHF2 |
| CH3 | OC2H5 |
| C6H5 | OCH3 |

EXAMPLE 3

General instructions for the manufacture of compounds of the formula I from 2-methylsulfonyl-4-methyl-5,6-dihydrofuran-[2,3-d]pyrimidine and lactic acid derivatives of the formula HX—CHR³—COOH:

1.57 g (14 mmol) of potassium tert-butylate is added to 7 mmol of a lactic acid derivative HX—CHR³—COOH in 15 ml of anhydrous dimethyl sulfoxide, and the mixture is stirred for 1 hour at room temperature. After the addition of 1.61 g (7 mmol) of 2-methylsulfonyl-4-methyl-5,6-dihydrofuran[2,3-d]pyrimidine the reaction mixture is stirred for 48 hours at room temperature and then introduced into 300 ml of water to which 2.5 ml of phosphoric acid has been added. Extraction is carried out with ethyl acetate, followed by drying over sodium sulfate, and the solvent is removed under reduced pressure. The crude product may if desired by purified by chromatography on silica gel. In the case of a solid, it can be further purified by recrystallization from a suitable solvent.

If a lactic acid derivative HX—CHR³—COR¹ in which R¹ does not bear an acidic proton is to be reacted, only one equivalent (7 mmol) of potassium tert-butylate is employed.

The compounds listed in the table below were prepared in accordance with these general directions.

TABLE 1

| No. | R¹ | R³ | Phys. data mp. [°C.] |
|---|---|---|---|
| 1 | OH | i-Propyl | 188–190 |
| 2 | OH | Cyclopropyl | |
| 3 | OH | 2-Phenyl-2-propyl | 285–286 |
| 4 | OH | 2-Butyl | |
| 5 | OH | tert.-Butyl | 170–173 |
| 6 | OH | Cyclopentyl | 134–135 |
| 7 | OH | Phenyl | |
| 8 | OH | Benzyl | 179–180 (L enantiomer) |
| 9 | OH | 1-Phenyl-1-ethyl | 135–137 |
| 10 | ONa | Benzyl | 123–127 |
| 11 | OH | 2-Hydroxy-1,1-dimethyl-ethyl | 151–153 (racemate) |
| 12 | OH | 2-Hydroxy-1,1-dimethyl-ethyl | 154–156 (D enantiomer) |
| 13 | O—CH2—C(CH3)2— | | 140–141 (racemate) |
| 14 | O—CH2—C(CH3)2— | | 134–136 (D enantiomer) |
| 15 | OCH3 | 2-Fluoro-2-propyl | oil |
| 16 | OH | 2-Fluoro-2-propyl | 165–169 |

Use Examples

The herbicidal action of the compounds I is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for postemergence treatment was 0.25 and 0.5 kg/ha.

The pots were set up in the greenhouse at temperatures specific to the plant species, viz., from 20° to 35° C., and from 10° to 25° C. The experiments were run for from 2 to 4 weeks. During this period the plants were tended and their reactions to the various treatments assessed.

The scale used for assessment was 0 to 100, 100 denoting non-emergence or complete destruction of at least the visible plant parts, and 0 denoting no damage or normal growth.

The plants used in the greenhouse experiments were as follows:

| Botanical name | Abbreviation |
| --- | --- |
| Glycine max. | GLMXA |
| Avena fatua | AVEFA |
| Amaranthus retroflexus | AMARE |
| Stellaria media | STEME |
| Sinapis alba | SINAL |
| Triticum aestivum | TRZAS |

A very good herbicidal action is achieved with 0.5 and 0.25 kg/ha of active ingredient, for example with Examples 5 and 6. Compound 5 has good selectivity in soybeans, and compound 6 has an excellent selective action in wheat.

We claim:

1. A glycol aldehyde or lactic acid derivative or a sulfur analog thereof of the formula I

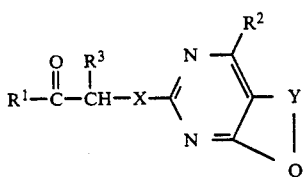

where
$R^1$ is
hydrogen;
succinylimidoxy;
a 5-membered heteroaromatic structure which is bonded via a nitrogen atom, contains two or three nitrogen atoms and may carry one or two halogen atoms or one or two of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
a radical

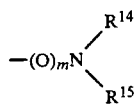

in which m is 0 or 1 and $R^{14}$ and $R^{15}$ are identical or different and are each
hydrogen;
$C_1$–$C_6$-alkyl, $C_3$–$C_6$-alkenyl or $C_3$–$C_6$-alkynyl, where these three radicals may each carry from one to five halogen atoms or one or two of the following groups: $C_1$–$C_6$-alkoxy, $C_3$–$C_6$-alkenyloxy, $C_3$–$C_6$-alkynyloxy, $C_1$–$C_6$-alkylthio, $C_3$–$C_6$-alkenylthio, $C_3$–$C_6$-alkynylthio, $C_1$–$C_6$-haloalkoxy, cyano, $C_1$–$C_6$-alkylcarbonyl, $C_3$–$C_6$-alkenylcarbonyl, $C_3$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, bis-$C_1$–$C_6$-dialkylamino, cyclo-$C_1$–$C_6$-alkyl or unsubstituted or substituted phenyl;
unsubstituted or substituted cyclo-$C_3$–$C_6$-alkyl; or unsubstituted or substituted phenyl; or $R^{14}$ together with $R^{15}$ form an unsubstituted or substituted, cyclized $C_4$–$C_7$-alkylene chain or together form an unsubstituted or substituted, cyclized $C_3$–$C_6$-alkylene chain having a hetero atom selected from the group consisting of oxygen, sulfur and nitrogen;
$R^1$ is furthermore a group

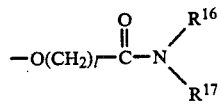

where $R^{16}$ and $R^{17}$ are identical or different and are each hydrogen, $C_1$–$C_6$-alkyl, unsubstituted or substituted phenyl, $C_3$–$C_6$-alkenyl or $C_3$–$C_6$-alkynyl and l is 1, 2, 3 or 4;
$R^1$ is furthermore a group

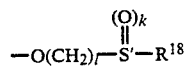

where $R^{18}$ is $C_1$–$C_6$-alkyl, unsubstituted or substituted phenyl, $C_1$–$C_6$-haloalkyl, $C_3$–$C_6$-alkenyl or $C_3$–$C_6$-alkynyl l is 1,2,3 or 4 and k is 0, 1 or 2;
$R^1$ is furthermore $OR^5$, where $R^5$ is
(a) hydrogen, an alkali metal cation, one equivalent of an alkaline earth metal cation, the ammonium cation or an organic ammonium ion;
(b) $C_3$–$C_{12}$-cycloalkyl which may carry from one to three $C_1$–$C_4$-alkyl radicals;
(c) $C_1$–$C_{10}$-alkyl which may carry from one to five halogen atoms or one of the following radicals: $C_1$–$C_4$-alkoxy, $C_1$–$C_4$-alkylthio, cyano, $C_1$–$C_4$-alkylcarbonyl, $C_3$–$C_{12}$-cycloalkyl, $C_1$–$C_8$-alkoxycarbonyl, phenyl, phenoxy or phenylcarbonyl, where the aromatic radicals in turn may each carry from one to five halogen atoms or from one to three of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
(d) $C_1$–$C_{10}$-alkyl which may carry from one to five halogen atoms and carries one of the following radicals: a 5-membered heteroaromatic structure containing from one to three nitrogen atoms or a 5-membered heteroaromatic structure containing one nitrogen atom and one oxygen or sulfur atom, which may carry from one to four halogen atoms or one or two of the following radicals: $C_1$–$C_4$- alkyl, $C_1-C_4$-haloalkyl, $C_1-C_4$-alkoxy, $C_1-C_4$-haloalkoxy or $C_1-C_4$-alkylthio;
(e) $C_2-C_6$-alkyl which carries one of the following radicals in the 2-position: $C_1-C_6$alkoximino, $C_3-C_6$-alkenyloximino, $C_3-C_6$-haloalkenyloximino or benzyloximino;
(f) $C_3-C_6$-alkenyl or $C_3-C_6$-alkynyl, where these groups in turn may carry from one to five halogen atoms;
(g) phenyl which may carry from one to five halogen atoms or from one to three of the following radicals; $C_1-C_4$-alkyl, $C_1-C_4$-haloalkyl, $C_1-C_4$-alkoxy, $C_1-C_4$-haloalkoxy or $C_1-C_4$-alkylthio;
(h) a 5-membered heteroaromatic structure which is bonded via a nitrogen atom, contains from one to three nitrogen atoms and may carry one or two halogen atoms or one or two of the following radicals: $C_1-C_4$-alkyl, $C_1-C_4$-haloalkyl, $C_1-C_4$-alkoxy, $C_1-C_4$-haloalkoxy or $C_1-C_4$-alkylthio;
(i) a group $-N=CR^6R^7$, where $R^6$ and $R^7$ are each $C_1-C_{20}$-alkyl which in turn may carry phenyl, $C_1-C_4$-alkoxy or $C_1-C_4$-alkylthio; or phenyl; or $R^6$ and $R^7$ together form a $C_3-C_{12}$-alkylene chain which may carry from one to three $C_1-C_3$-alkyl groups;

$R^1$ is furthermore a radical

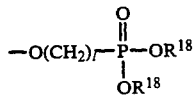

where $R^{18}$ and l have the abovementioned meanings, $R^1$ is furthermore a radical

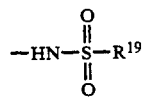

where $R^{19}$ is $C_1-C_6$-alkyl or phenyl which in turn may carry from one to four of the following substituents: halogen, nitro, cyano, $C_1-C_6$-alkyl;

$R^2$ is halogen, $C_1-C_4$-alkyl, $C_1-C_4$-haloalkyl, $C_1-C_4$-alkoxy, $C_1-C_4$-haloalkoxy or $C_1-C_4$-alkylthio;

$R^3$ is
hydrogen;
$C_1-C_8$-alkyl, $C_2-C_8$-alkenyl, $C_2-C_8$-alkynyl, phenyl, $C_3-C_8$-cycloalkenyl or $C_3-C_8$-cycloalkyl, each of which may carry from one to five halogen atoms and, independently of one another, from one to three of the following substituents:
(i) hydroxyl, $C_1-C_4$-haloalkyl, $C_1-C_4$-alkoxy, $C_1-C_4$-alkylthio, cyano, nitro, $C_1-C_4$-alkoxycarbonyl, $C_1-C_4$-alkylcarbonyl, $C_1-C_4$-alkyl, phenylcarbonyl, $C_3-C_{12}$-cycloalkyl, $C_3-C_{12}$-cycloalkenyl;
(ii) a 5-membered heterocyclic structure containing no double bonds or one or two double bonds and from one to four nitrogen atoms or one or two nitrogen atoms and additionally one sulfur or oxygen atom, which may carry from one to three halogen atoms or from one to three of the following radicals: nitro, cyano, $C_1-C_4$-alkyl, $C_1-C_4$-alkoxy, $C_1-C_4$-alkylthio, $C_1-C_4$-haloalkyl or phenyl, which in turn may carry from one to three halogen atoms or from one to three methyl groups;
(iii) thienyl which may carry from one to three halogen atoms or from one to three of the following radicals: $C_1-C_4$-alkyl, $C_1-$ or $C_2$-haloalkyl and nitro;
(iv) pyridyl which may carry from one to three halogen atoms or from one to three of the following radicals: $C_1-C_4$-alkyl, $C_1-$ or $C_2$-haloalkyl or nitro;
(v) naphthyl, quinolyl, benzoxazolyl, benzothiazolyl, benzothienyl, indazolyl or benzotriazolyl, each of which may carry from one to three halogen atoms or from one to three of the following radicals: $C_1-C_4$-alkyl and $C_1-$ or $C_2$-haloalkyl;
(vi) phenyl which in turn may carry from one to five halogen atoms or from one to three of the following radicals: $C_1-C_4$-alkyl, $C_1-C_4$-alkoxy, $C_1-C_4$-haloalkyl, $C_1-C_4$-haloalkoxy, cyano, nitro, $C_1-C_4$-dialkylamino or $C_1-C_4$-alkylthio;
(vii) a 5-membered or 6-membered heterocyclic structure containing no double bonds or one or two double bonds and one or two oxygen or sulfur atoms, which may furthermore carry the following radicals: $C_1-C_4$-alkyl, $C_1-C_4$-alkoxy, $C_1-C_4$-haloalkyl, $C_1-C_4$-haloalkoxy or nitro;

$R^3$ may furthermore be a 5-membered heterocyclic structure containing no double bonds or one or two double bonds and from one to four nitrogen atoms or one or two nitrogen atoms and additionally one sulfur or oxygen atom, which may carry from one to three halogen atoms or from one to three of the following radicals: nitro, cyano, $C_1-C_4$-alkyl, $C_1-C_4$-alkylthio, $C_1-C_4$-haloalkyl, $C_1-C_4$-haloalkoxy, $C_1-C_4$-alkoxy or phenyl, which in turn may carry from one to three halogen atoms or from one to three methyl groups; or $R^3$ is a 6-membered heterocyclic structure selected from the group consisting of morpholin-1-yl, 3,5-dimethylmorpholin-1-yl and 1-piperidyl, a 5-membered heterocyclic structure containing no double bonds or one or two double bonds and one or two oxygen or sulfur atoms, which may furthermore carry the following radicals: halogen, nitro, $C_1-C_4$-alkyl, $C_1-C_4$-alkoxy, $C_1-C_4$-haloalkyl or $C_1-C_4$-haloalkoxy; $R^3$ together with $R^1$ are an unsubstituted or substituted $C_4-C_7$-alkylene chain where $CH_2$ may be replaced by oxygen sulfur or nitrogen;

X is oxygen, sulfur or a single bond and

Y is a $C_2-C_4$-alkylene or $C_2-C_4$-alkenylene chain where in each case a methylene group may be substituted by an oxo group ($aO$) and/or where the alkylene or alkenylene chain may be substituted by $C_1-C_4$-alkyl, phenyl, $C_1-C_4$-alkoxy or $C_1-C_4$-alkoxycarbonyl;

in the abovementioned cases the expression unsubstituted or substituted meaning in each case that the groups so referred to may carry one or more of the following substituents: halogen, nitro, cyano, $C_1-C_6$-alkyl, $C_1-C_6$-haloalkyl, $C_1-C_6$-alkoxy and $C_1-C_6$alkylthio, and environmentally compatible salts of the compound I.

2. A glycol aldehyde or lactic acid derivative of the formula I as defined in claim 1, wherein $R^2$ is methoxy, X is oxygen and $R^1$ and $R^3$ have the meanings stated in claim 1.

3. A lactic acid derivative of the formula I as defined in claim 1, wherein $R^1$ is $OR^5$, $R^5$ is hydrogen, $C_1-C_{10}$-alkyl, benzyl, $C_3-C_6$-alkenyl or $C_3-C_6$-alkynyl, $R^2$ is methoxy, $R^3$ is hydrogen or $C_1-C_6$-alkyl which may be substituted as stated in claim 1, X is oxygen or sulfur and Y is a $C_2H_4$ chain.

4. A lactic acid derivative of the formula I as defined in claim 1, wherein $R^1$ is $OR^5$, $R^5$ is a group $-N=CR^6R^7$, where $R^6$ and $R^7$ are each $C_1-C_4$-alkyl which is unsubstituted or substituted by phenyl, $C_1-C_4$-alkoxy or $C_1-C_4$-alkylthio, or are each phenyl, or $R^6$ together with $R^7$ forms a $C_3-C_6$-alkylene chain which may be substituted by $C_1-C_3$-alkyl, $R^2$ is methoxy, $R^3$ is hydrogen or $C_1-C_8$-alkyl which may be substituted as stated in claim 1, X is oxygen or sulfur and Y is a $C_2H_4$ chain.

5. A herbicidal composition containing a compound of the formula I as defined in claim 1 and conventional inert additives.

6. A herbicidal composition containing conventional inert additives and a compound of the formula I as defined in claim 1 wherein $R^1$ is $OR^5$, $R^5$ is hydrogen, $C_1-C_{10}$-alkyl, benzyl, $C_3-C_6$-alkenyl or $C_3-C_6$-alkynyl, $R^2$ is methoxy, $R^3$ is hydrogen or $C_1-C_8$-alkyl which may be substituted as stated in claim 1, X is oxygen or sulfur and Y is a $C_2H_4$ chain.

7. A method for controlling undesirable plant growth, wherein a herbicidal amount of a compound of the formula I as defined in claim 1 is allowed to act on the plants or on their habitat.

8. A method for regulating plant growth, wherein a bioregulatory amount of a compound of the formula I as defined in claim 1 is allowed to act on the plants or on their habitat.

9. A plant growth regulating composition containing a compound of the formula I as defined in claim 1 and conventional inert additives.

10. A plant growth regulating composition containing conventional inert additives and a compound of the formula I as claimed in claim 1 wherein $R^1$ is $OR^5$, $R^5$ is hydrogen, $C_1-C_{10}$-alkyl, benzyl, $C_3-C_6$-alkenyl or $C_3-C_6$-alkynyl, $R^2$ is methoxy, $R^3$ is hydrogen or $C_1-C_8$-alkyl which may be substituted as stated in claim 1, X is oxygen or sulfur and Y is a $C_2H_4$ chain.

* * * * *

UNITED STATES PATENT AND TRADEMARK OFFICE
CERTIFICATE OF CORRECTION

PATENT NO.: 5,326,744

DATED: July 5, 1994

INVENTOR(S): RHEINHEIMER et al.

It is certified that error appears in the above-identified patent and that said Letters Patent is hereby corrected as shown below:

Column 24, claim 1, line 4, "$C_1C_6$-alkyl" should read --$C_1$-$C_6$-alkyl--.

Column 24, claim 1, line 53, after "cyano", "$C_1$-$C_4$-" should read -- $C_1$-$C_8$- --.

Column 25, claim 1, line 4, "$C_1$-$C_6$alkoximino" should read --$C_1$-$C_6$-alkoximino--.

Column 26, claim 1, line 51, "($\alpha$0)" should read --(=0)--.

Column 26, claim 1, line 58, after "and", "$C_1$-$C_6$al-" should read -- $C_1$-$C_6$-al- --.

Column 26, claim 2, line 68, "$C_1$-$C_6$-alkyl" should read --$C_1$-$C_8$-alkyl--.

Signed and Sealed this

Fifteenth Day of November, 1994

Attest:

BRUCE LEHMAN

Attesting Officer     Commissioner of Patents and Trademarks